(12) United States Patent
Lois

(10) Patent No.: US 8,529,481 B1
(45) Date of Patent: Sep. 10, 2013

(54) APPENDAGE COVERING SYSTEM

(76) Inventor: William A Lois, Brooklyn, NY (US)

( * ) Notice: Subject to any disclaimer, the term of this patent is extended or adjusted under 35 U.S.C. 154(b) by 632 days.

(21) Appl. No.: 11/828,988

(22) Filed: Jul. 26, 2007

(51) Int. Cl.
*A61F 5/00* (2006.01)

(52) U.S. Cl.
USPC .......................................................... 602/3

(58) Field of Classification Search
USPC ....... 602/3, 79; 2/16, 22; D24/190; D2/901; 604/180
See application file for complete search history.

(56) References Cited

U.S. PATENT DOCUMENTS

| | | | | | |
|---|---|---|---|---|---|
| 3,741,203 | A | * | 6/1973 | Liman | 602/3 |
| 4,646,727 | A | * | 3/1987 | Chambers | 602/3 |
| 5,083,557 | A | * | 1/1992 | Lennon et al. | 602/3 |
| 5,592,953 | A | * | 1/1997 | Delao | 128/882 |
| 5,817,038 | A | * | 10/1998 | Orange et al. | 602/3 |
| 5,924,130 | A | * | 7/1999 | Fragomeli | 2/16 |
| 6,895,971 | B1 | * | 5/2005 | Evans | 128/869 |
| 6,941,579 | B2 | * | 9/2005 | Tanenbaum | 2/123 |
| 7,302,711 | B1 | * | 12/2007 | Tanenbaum | 2/162 |
| 2005/0020949 | A1 | * | 1/2005 | Switzer et al. | 602/3 |
| 2007/0088281 | A1 | * | 4/2007 | Ritchey | 604/174 |

* cited by examiner

*Primary Examiner* — Kim M Lewis
(74) *Attorney, Agent, or Firm* — Michael I. Kroll

(57) ABSTRACT

A system for protecting the appendage of a user from contamination and water seepage while bathing or outdoors during inclement weather. The system includes a protective cover and a sleeve. The protective cover is sized and configured for placement about the hand and arm or the foot and leg of a user. The cover includes a slit with a zipper closure and may include a closure flap at the upper end of the slit. The cover may include securing straps for retaining the cover securely about the appendage of the user. The sleeve extends over and covers the open end of the cover to provide an additional barrier against contamination and seepage.

5 Claims, 13 Drawing Sheets

APPENDAGE COVERING SYSTEM

BACKGROUND OF THE INVENTION

1. Field of the Invention

The present invention relates generally to a protective covering for a bandage or a cast, or more specifically to a protective covering with an opening for inserting an appendage and a slit extending longitudinally from the opening to provide a larger opening to make it easier for the user to place the covering over their appendage.

2. Description of the Prior Art

There are other protective devices designed for cast/bandage coverings. While these protective devices may be suitable for the purposes for which they were designed, they would not be as suitable for the purposes of the present invention, as hereinafter described.

Therefore it is felt that a need exists for a two-part protective covering for a bandage or cast that can be used in conjunction with each other to prevent water damage and contamination to the bandage/cast.

SUMMARY OF THE PRESENT INVENTION

A primary object of the present invention is to provide a protective covering for a bandage or cast allowing the user to take a shower and to travel in inclement weather without contaminating or damaging the bandage or cast.

Another object of the present invention is to provide a protective bandage or cast covering having an opening for inserting an appendage.

Another object of the present invention is to provide a seal member about the opening so that the where the covering is in place on the user's users appendage the opening is sealed about the appendage.

Another object of the present invention is to provide a protective covering having a longitudinal slit with a closure mechanism positioned along the slit.

Yet another object of the present invention is to provide a protective bandage or cast covering where the closure mechanism is a slider for opening and closing the longitudinal slit.

Another object of the present invention is to provide a protective bandage or cast covering having a mitten shape portion to receive the user's hand and allow use of the hand, such as when taking a shower.

Yet another object of the present invention is to provide a protective bandage or cast covering having a foot shaped portion to receive the user's foot where the foot shaped portion has at one non-slip surface.

Still yet another object of the present invention is to provide a sleeve with elastic ends and optional sealing members where the sleeve is used in conjunction with the protective bandage or cast covering to further seal the protective bandage or cast from damage.

Another object of the present invention is to optionally provide the sleeve with a slit and integral closure mechanism.

Additional objects of the present invention will appear as the description proceeds.

The present invention overcomes the shortcomings of the prior art by providing a system for protecting a bandage or cast from contamination and damage including a protective covering and a sleeve. The protective covering has a sealing member lining an aperture that receives the user's appendage and includes a slit extending longitudinally along the covering from the opening and incorporates a closure mechanism for opening and closing the slit in a relatively water tight seal. The sleeve is provided as a secondary sealing member over the open end of the protective cover. The sleeve has elastic ends where each end is provided with a sealing member where one seals against the user's users appendage and the other seals against the protective cover to act as a secondary seal about the users appendage. The sleeve optionally provided with a zippered slit similar to that of the protective covering.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

LIST OF REFERENCE NUMERALS

Figure 1:
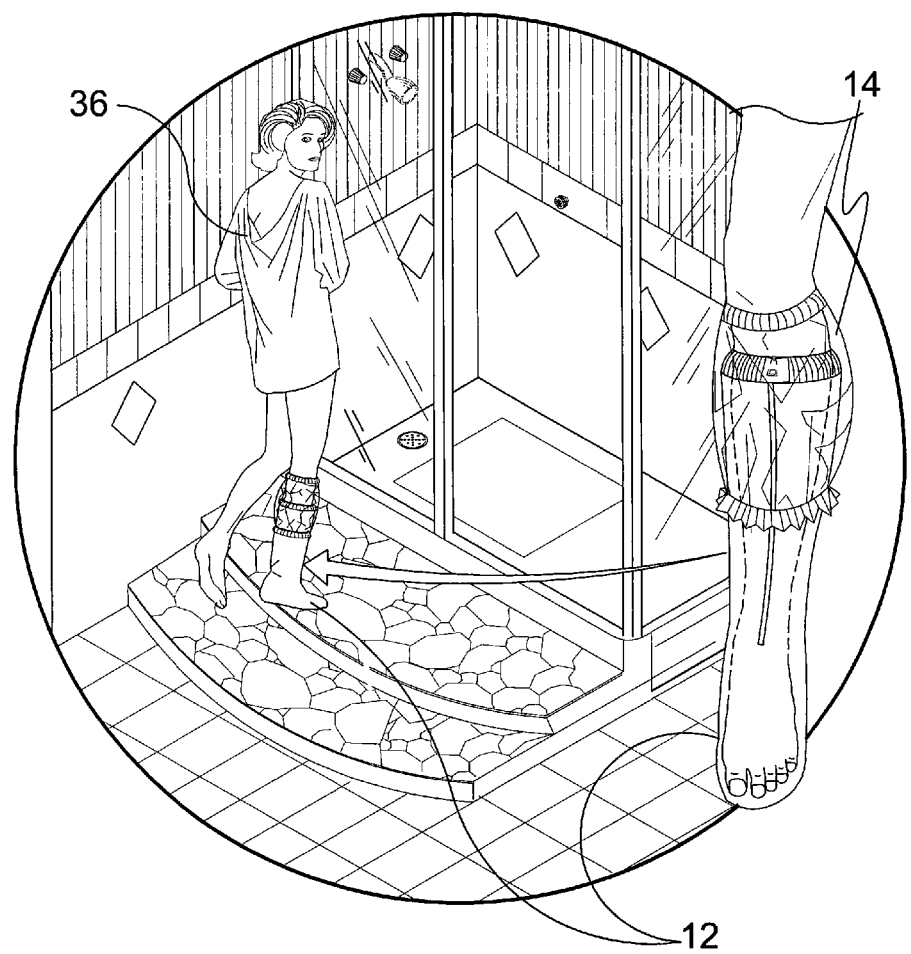
FIG. 1 is an illustrative view of the present invention in use.

With regard to reference numerals used, the following numbering is used throughout the drawings.

10 Appendage covering system
12 Appendage cover
14 Sleeve
16 Opening
18 Slit
20 Zipper
22 Slider
24 Elastic band
26 Closure flap
28 Hook and loop strips
30 Foot portion
32 Hand portion 34 Bandage
36 User
38 Sealing member
40 Leg
42 arm
44 Anti-slip material
46 Securing strap

DETAILED DESCRIPTION OF THE PREFERRED EMBODIMENT

The present invention will be described more fully hereafter with reference to the accompanying drawings, in which preferred embodiments of the invention as shown. This invention may, however be embodied in many different forms and should not be construed as limited to the embodiments set forth herein; rather, these embodiments are provided so that the disclosure will be thorough and complete, and will fully convey the scope of the invention to those skilled in the art. Like numbers refer to like components throughout, and some dimensions and thicknesses may be exaggerated for clarity.

Referring now to the drawings, the appendage covering system 10 of the present invention is illustrated in FIGS. 1 through 13. The appendage protection system of the present invention includes an appendage cover 12 and a sleeve 14. These items are shown on a user prior to entering the shower in FIG. 1. The appendage cover 12 is an enclosure or garment for placement over an appendage of the user 36. The appendage cover 12 encloses a cast, bandage 34, or fixation device on the user's 36 appendage to protect them from contamination or damage. The appendage cover 12 is made of an impermeable (i.e. waterproof) plastic material shaped to fit the leg or arm of the user 36. The plastic may be a polymer or a copolymer or blends thereof and may employ a single layer or multiple layers. The cover 12 has an opening 16 (i.e. open end) for receiving the user's 36 appendage there through. The cover 12 is preferably provided with a slit 18 extending from the opening 16 to provide a larger access opening for the user's 36 appendage where the slit 18 may be closed by a zipper 20.

Figure 13:
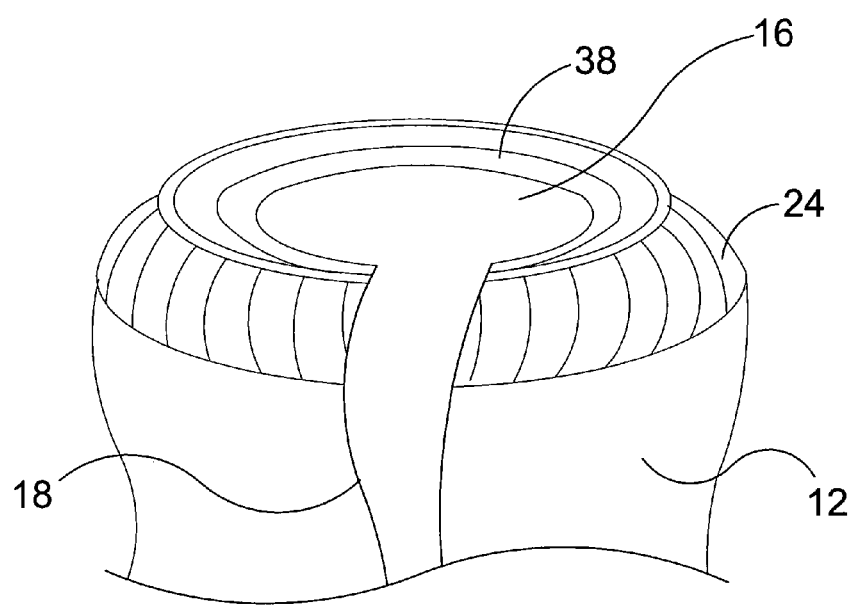
FIG. 13 is a partial view of the cover showing a sealing member.

The zipper 20 may be provided with a slider 22 to make it easier for the user to open and close. It is envisioned that the zipper may be in the form of a rib and groove closure similar to those found on storage bags. One possible zipper is found in U.S. Pat. No. 2,613,321 to Madsen, which is incorporated herein by reference in its entirety. The rib and groove strips may be formed in one piece with the cover or they may be on strips separate from the cover where the strips are then secured to the slit on the cover. The interlocking rib and groove closures provide an excellent leak proof seal. The zipper 20 need not be a rib and groove closure but may be any closure that is capable of providing a leak proof or water tight seal. The opening 16 or open end is provided with an elastic band 24 to seal around the user's limb or appendage, preventing water from entering. The purpose of the system 10 of the present invention is to allow patients with wounds, casts, or fixation devices the freedom to take showers and go into inclement weather (rain or snow) without damaging the cast or contaminating their dressing. The appendage cover 12 may be provided with a fastener at its open end to form a more effective seal against water seepage. The fastener may be in the form of a closure flap 26 with hook and loop strips 28 (i.e. Velcro, see FIG. 3). The open end of the cover 12 may be provided with a sealing member 38 on the interior surface thereof to aid in sealing between the cover 12 and the user's 36 appendage (see FIG. 13). In FIG. 13 the protective cover is shown without the closure flap and the zipper for clarity. The sealing member may be made of a resilient foamed plastic, silicone, rubber, or other suitable material. This material may be secured to the cover 12 by heat sealing, adhesive or other suitable methods.

Figure 4:
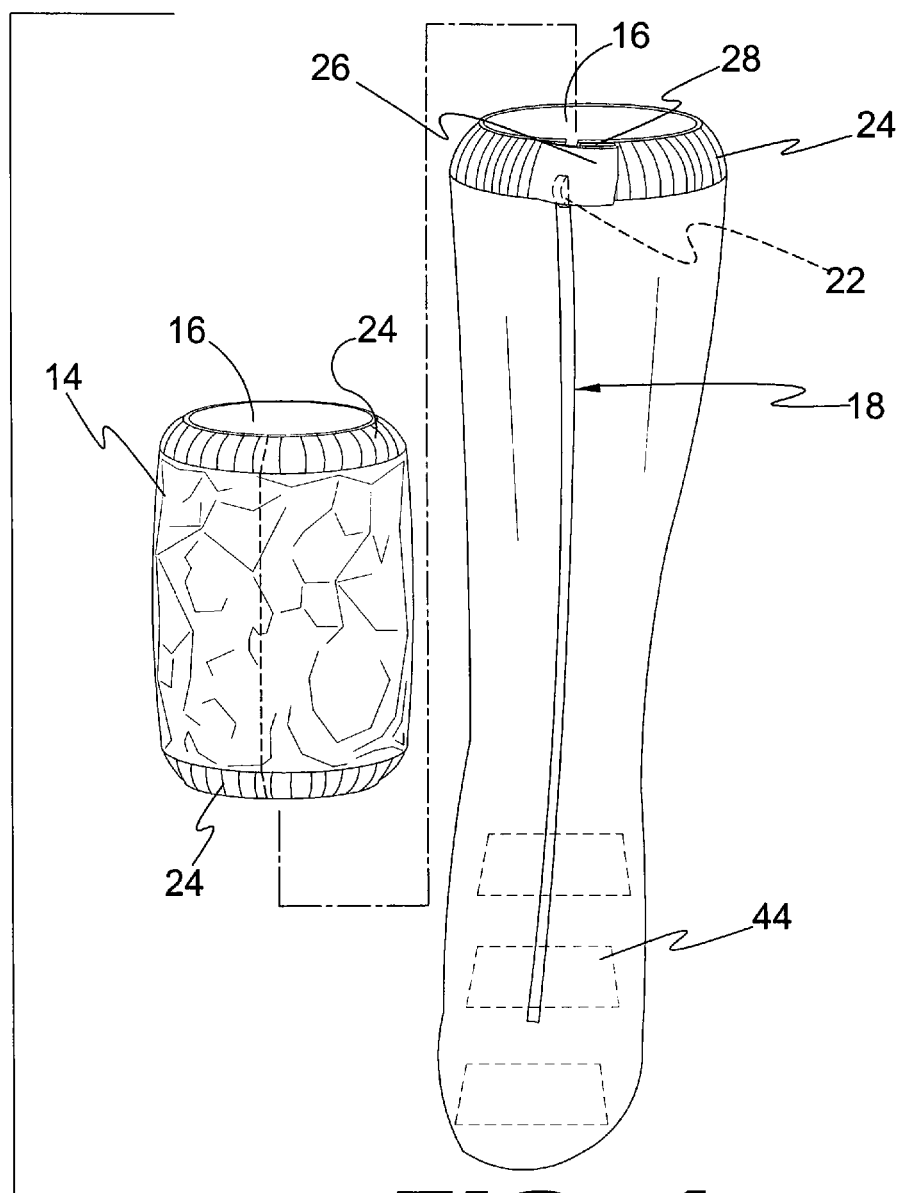
FIG. 4 is a perspective frontal view of the present invention.
Figure 5:
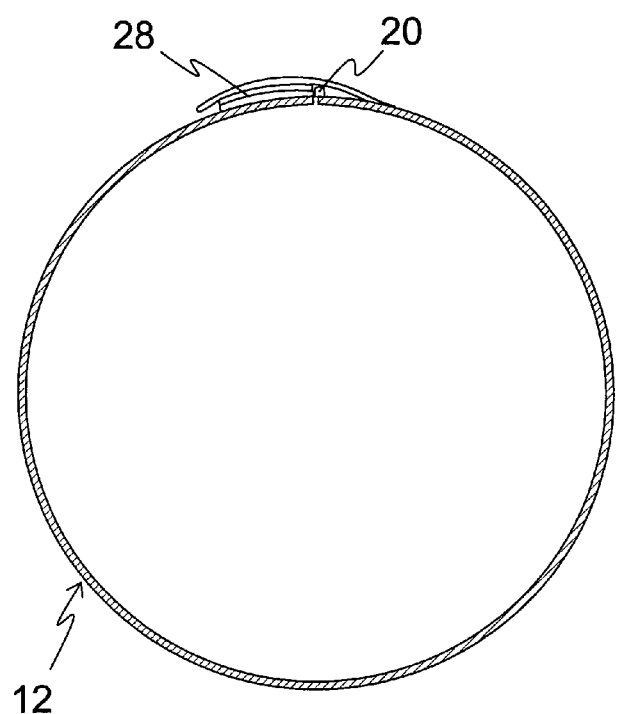
FIG. 5 is a sectional view of the present invention.
Figure 6:
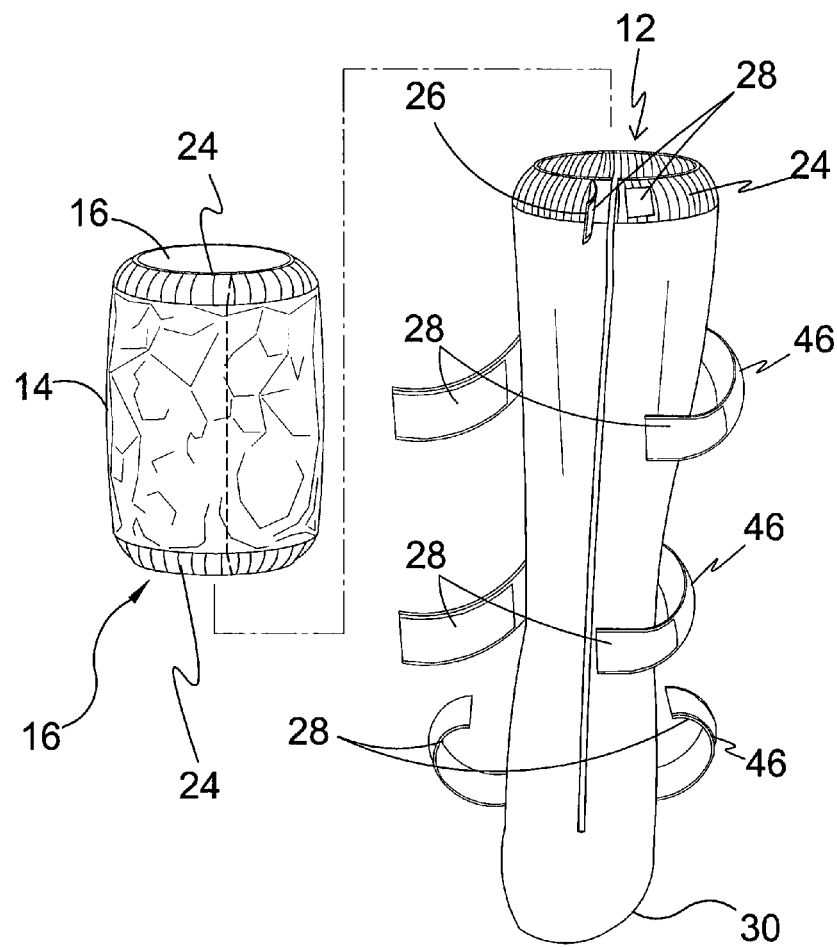
FIG. 6 is a frontal view of a second embodiment of the present invention for use on legs.
Figure 7:
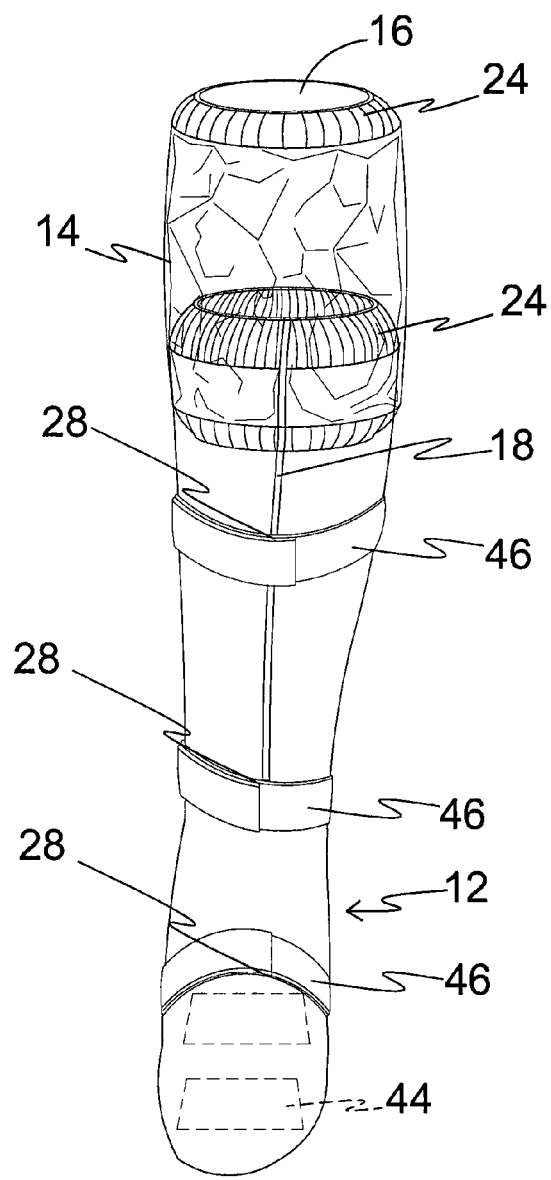
FIG. 7 is a frontal view of a second embodiment of the present invention for use on legs.
Figure 8:
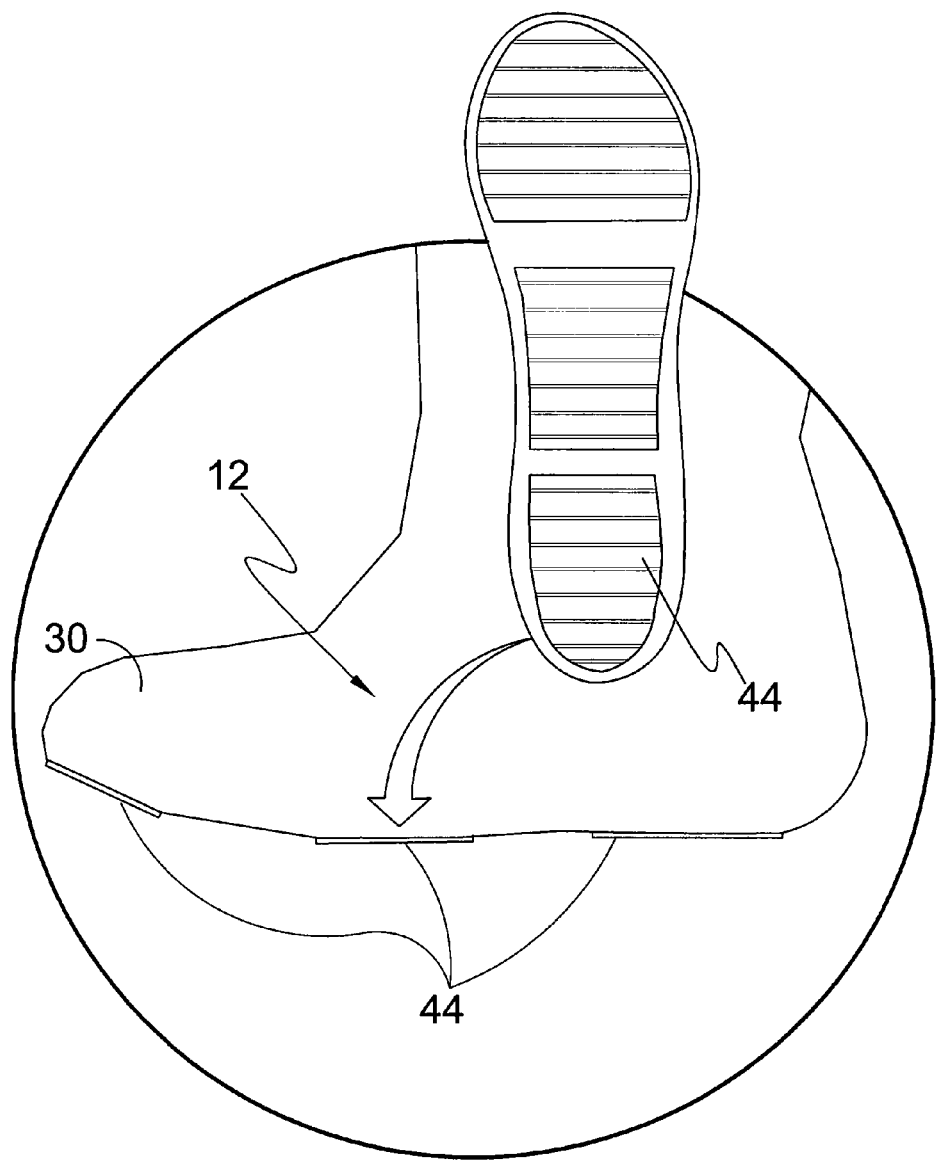
FIG. 8 is a detailed view of the present invention.

The appendage cover 12 may be used in lieu of or in combination with a sleeve 14. The sleeve 14 is made of an impermeable (i.e. waterproof) plastic material and has elastic bands 24 at each end. The sleeve 14 may be formed of the same material as the cover or a different material. The sleeve 14 has openings 16 at each end to allow the appendage of the user to pass there through. The sleeve 14 is placed over the open end of the appendage cover 12 (see best in FIGS. 3, 7, and 10) so that one end seals against the appendage cover 12 and the other end seals against the appendage of the user 36. The sleeve 14 provides an additional barrier against water seepage. At least one open end of the sleeve 14 may be provided with a sealing member 38 on the interior surface thereof (see FIG. 12) to aid in sealing about the appendage of the user 36 and the cover 12. It is envisioned that each open end may be provided with a sealing member 38. The sealing members 38 may be made of a resilient foamed plastic, silicone, rubber, or other suitable material. This material may be secured to the sleeve 12 by heat sealing, adhesive or other suitable methods. The sleeve may be made of a tubular plastic extrusion (i.e. seamless) or the sleeve may be made of a sheet material with a seam. The seam is shown in FIGS. 4 and 6 by the dotted line. The ends of the sheet may be joined together at the seam by heat sealing, adhesive or any other suitable means provided that it produces a water tight seam.

Figure 2:
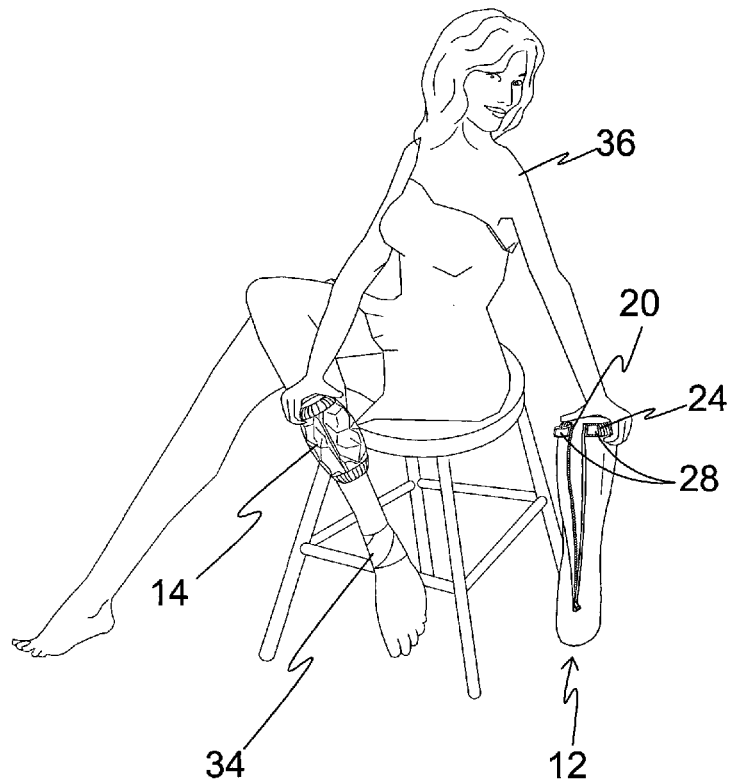
FIG. 2 is an illustrative view of the present invention in use.
Figure 3:
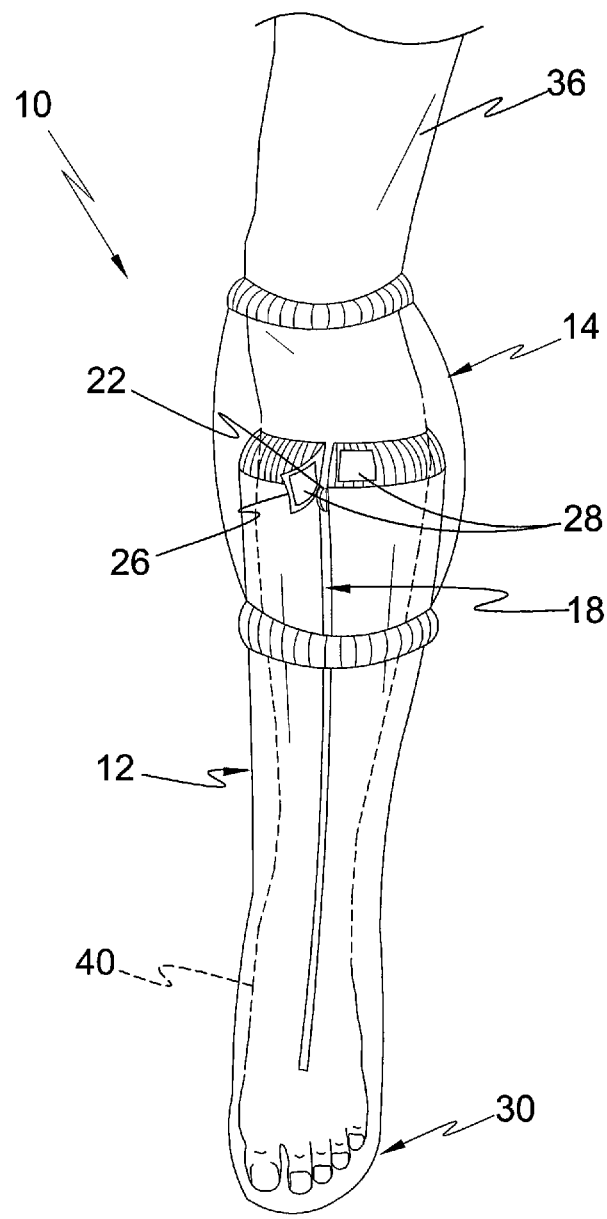
FIG. 3 is an illustrative frontal view of the present invention in use.
Figure 9:
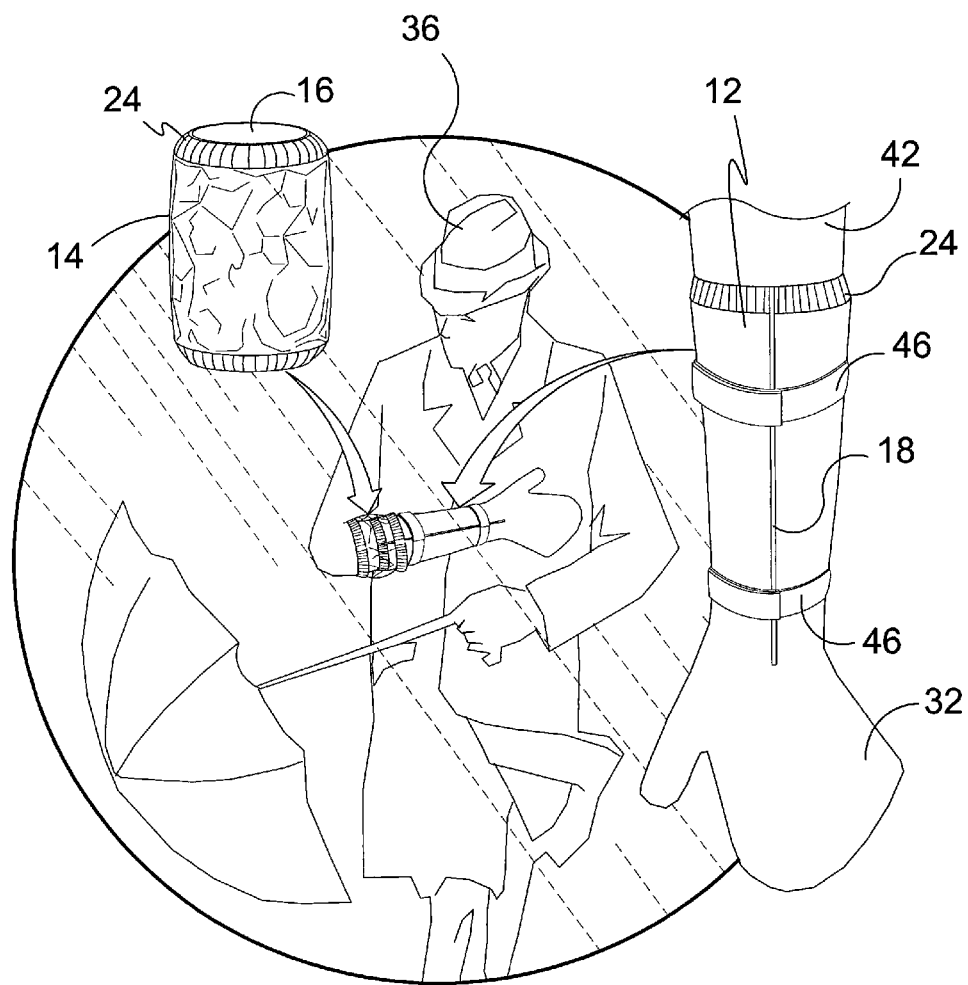
FIG. 9 is an illustrative view of a third embodiment of the present invention for use on arms.
Figure 10:
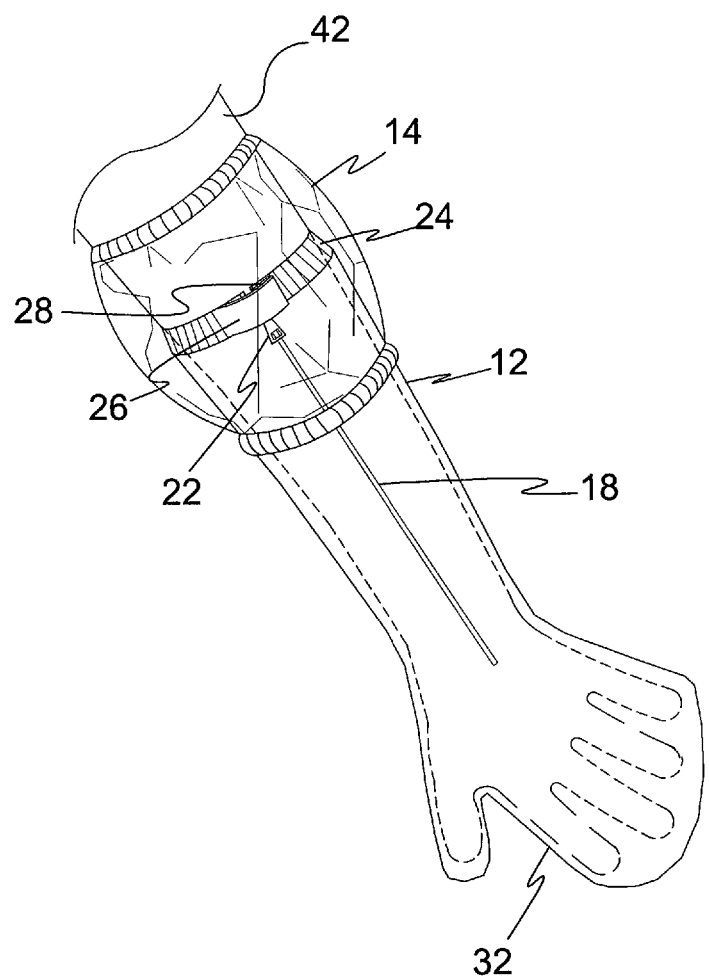
FIG. 10 is an illustrative view of a third embodiment of the present invention having a zipper closure.
Figure 11:
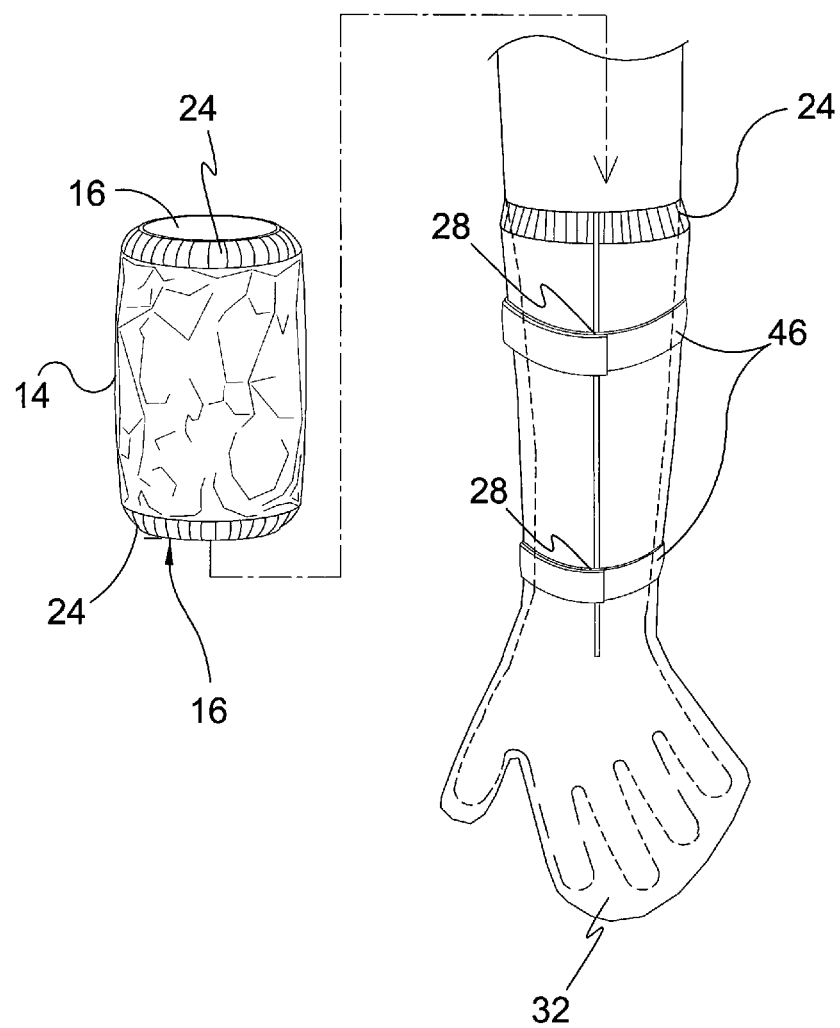
FIG. 11 is an illustrative view of a third embodiment of the present invention having Velcro® straps for closure.
Figure 12:
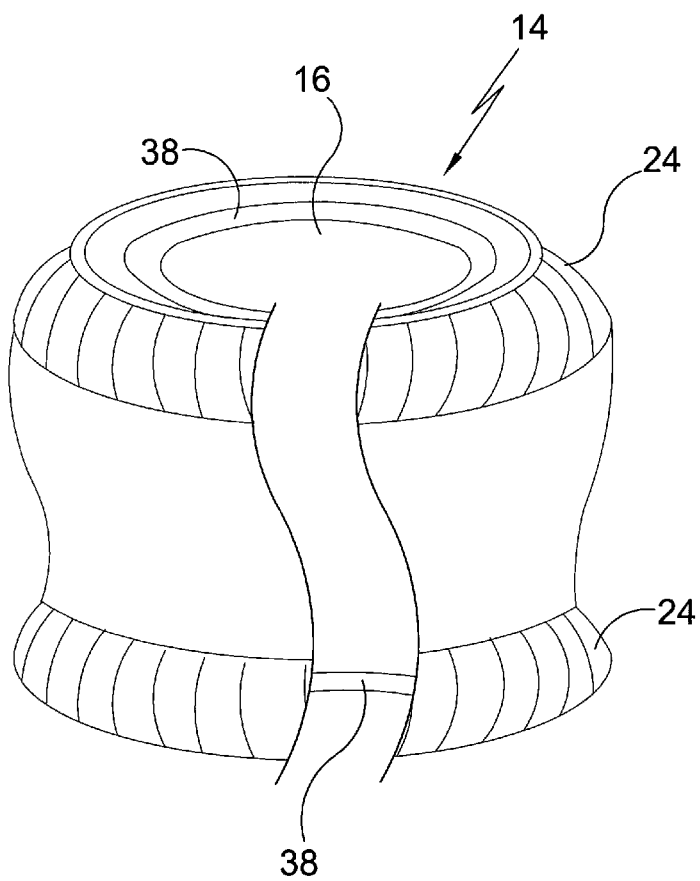
FIG. 12 is a partial view of the sleeve showing a sealing member.

One way of deploying the system of the present invention is shown in FIG. 2. The user 36 has first placed the sleeve 14 over their leg 40 (see FIG. 2) that has a bandage 34 covering a wound. Once the sleeve 14 is in place, the user 36 then inserts their foot and leg 40 into the protective cover 12. Once the zipper 20 on the slit 18 is closed and the closure flap 26 at the opening 16 (i.e. open end) is secured, the user 36 lowers the sleeve 14 over the open end of the cover 12 (see FIG. 3). The foot portion 30 of the protective cover 12 may be provided with anti-slip material 44 (see FIGS. 4, 7, and 8) to provide the user with traction on wet and or slippery surfaces. The anti-slip material 44 may be provided in strips on the bottom surface of the foot portion or it may cover the entire bottom surface of the foot portion. The anti-slip material 44 may be made of a resilient plastic, natural rubber, synthetic rubber, silicone, thermoplastic elastomers, or other suitable materials. As seen in FIGS. 1-8, one form of the protective cover 12 is for the foot and leg 40 of a user 36. Another form of the protective cover is shown in FIGS. 9-11, which is for the hand and arm 42 of the user 36. The protective cover 12 has a closed end that is opposite the opening 16. The closed end is formed into either a foot portion 30 (see FIG. 8) or a hand portion 32 (see FIG. 10).

The protective cover 12 of the present invention 10 may be provided with at least one or more securing straps 46 for maintaining the cover 12 about the appendage of the user 36. These straps 46 are seen in FIGS. 6, 7, 9, and 11 and may be provided on either form of the present invention (i.e. foot and leg cover or hand and arm cover). The securing straps 46 shown are provided with hook and loop strips 28 (commonly referred to as Velcro®). The present invention may employ other fastening mechanisms on the securing straps 46. These may include but are not limited to snaps, buckles, or any other suitable fastening mechanism.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the claims, with equivalents of the claims to be included therein.

I claim:

1. A system for protecting a cast or bandage from moisture on a user's appendage, the system consisting:
   a) a cover of impermeable material sized and configured for receiving the user's appendage and enclosing said cast or bandage, the cover having an open end and a closed end for enclosing a distal end of said appendage, the open end being capable of receiving the appendage therethrough and the open end is capable of being secured about the users appendage, a slit extending from the open end and terminating short of said closed end, the slit having a closure that is capable of closing the slit in a water-tight manner;
   b) a sleeve of water impermeable material enclosing a portion of said cover including said open end of said cover, said sleeve being open at a first end and an opposite end, said sleeve being permanently fully enclosed between said ends thereof;
   c) said sleeve extending between a mid portion of said cover and passing over and past the open end of said cover and terminating at an opposite end thereof at a point beyond said open end of said cover, said sleeve having an elastic band along an edge of each open end of said sleeve for sealing said first end against said cover and the opposite end adapted to seal the open end thereof on said appendage, said sleeve having an exposed sealing member on an inner surface of said edge of each open end of said sleeve to aid in sealing said sleeve at each end to cover and the appendage, said sleeve being unfolded;
   d) the elastic band at each open end of said sleeve being made of a resilient material selected from a group consisting of a foamed plastic, silicone and rubber, said exposed sealing members providing increased sealing at the open ends;
   e) wherein the open end of the cover is provided with elastic;
   f) wherein the cover has a closure flap disposed on the elastic at the open end of said cover; and
   g) wherein the cover has at least one securing strap intermediate the closed and open ends.

2. The system of claim 1, wherein said distal end is shaped to fit a hand of said user.

3. The system of claim 1, wherein said distal end is shaped to fit a foot of said user.

4. A method of protecting a cast or bandage from moisture on a user's limb consisting of the steps of:
   a) pulling a sleeve on said limb completely past said cast or bandage, said sleeve being of water impermeable material and being open at both ends thereof, said sleeve being permanently fully enclosed between said ends thereof;
   b) placing a cover of impermeable material on said limb enclosing said cast or bandage, the cover having an open end and a closed end enclosing a distal end of said limb, a slit extending from the opening end and terminating short of said closed end, the slit having a closure that is capable of closing the slit in a water-tight manner; and
   c) drawing said sleeve over the open end of said cover, said sleeve having an elastic band along an edge of each open end of said sleeve, one end sealed on said cover in a mid portion of said cover and an opposite end adapted to seal on said limb, said sleeve overlapping the open end of said cover and terminating at a point beyond said cover open end, said sleeve being unfolded, the open ends of said sleeve each having attached on an inside surface thereof at said ends with an exposed sealing member of a resilient material selected from a group consisting of a foamed plastic, silicone and rubber, said resilient material directly inwardly to provide increased sealing of a region enclosed by said sleeve.

5. A system for protecting a cast or bandage from moisture on a user's appendage, the system consisting of:
   a) a cover of impermeable material having an open end and a closed end for enclosing said cast or bandage and a distal end of said appendage;
   b) a sleeve of water impermeable material open at both ends extending between a mid portion of said cover and passing over and past the open end of said cover and terminating at an opposite end thereof at a point beyond said open end of said cover; and
   c) a sealing member on an interior surface of said sleeve adjacent each end opening to aid in sealing said sleeve at each end to said appendage and said cover, an elastic band on the exterior surface of said sleeve adjacent each end.

* * * * *